United States Patent
Chudzik et al.

(10) Patent No.: US 7,820,158 B2
(45) Date of Patent: Oct. 26, 2010

(54) LIGAND-COUPLED INITIATOR POLYMERS AND METHODS OF USE

(75) Inventors: Stephen J. Chudzik, St. Paul, MN (US); Dale G. Swan, St. Louis Park, MN (US)

(73) Assignee: SurModics, Inc., Eden Prairie, MN (US)

( * ) Notice: Subject to any disclaimer, the term of this patent is extended or adjusted under 35 U.S.C. 154(b) by 916 days.

(21) Appl. No.: 10/412,063

(22) Filed: Apr. 10, 2003

(65) Prior Publication Data

US 2004/0203075 A1   Oct. 14, 2004

(51) Int. Cl.
  *A61K 9/50*   (2006.01)
  *C12N 5/00*   (2006.01)
  *C12N 11/04*  (2006.01)

(52) U.S. Cl. ............... 424/93.7; 424/78.08; 424/78.17; 424/193.1; 424/194.1; 435/7.1; 435/174; 514/592; 514/601; 516/150; 516/911; 522/87; 522/88; 522/904; 623/920

(58) Field of Classification Search .................. 435/7.1, 435/4, 182, 173.4, 180, 181, 174; 424/418, 424/486, 78.18, 78.08, 78.17, 193.1, 194.1, 424/93.7; 514/592, 593, 595, 601; 522/87, 522/88, 904; 523/200, 300; 527/202; 564/39, 564/40, 42, 43; 516/150, 911; 623/920
See application file for complete search history.

(56) References Cited

U.S. PATENT DOCUMENTS

| | | | |
|---|---|---|---|
| 4,908,404 A | 3/1990 | Benedict | |
| 5,332,475 A * | 7/1994 | Mechanic | 204/157.68 |
| 5,410,016 A | 4/1995 | Hubbell et al. | |
| 5,494,940 A * | 2/1996 | Unger et al. | 521/66 |
| 5,529,914 A | 6/1996 | Hubbell et al. | |
| 5,573,934 A | 11/1996 | Hubbell et al. | |
| 5,779,673 A * | 7/1998 | Roth et al. | 604/101.03 |
| 5,834,274 A | 11/1998 | Hubbell et al. | |
| 5,858,653 A | 1/1999 | Duran | |
| 5,897,955 A * | 4/1999 | Drumheller | 428/422 |
| 6,007,833 A | 12/1999 | Chudzik et al. | |
| 6,060,582 A | 5/2000 | Hubbell et al. | |
| 6,169,100 B1 * | 1/2001 | Ikeda et al. | 514/342 |
| 6,258,870 B1 | 7/2001 | Hubbell et al. | |
| 6,410,044 B1 | 6/2002 | Chudzik et al. | |

(Continued)

FOREIGN PATENT DOCUMENTS

WO   WO 01/85180   11/2001

OTHER PUBLICATIONS

Schwanstecher, M. et al. Photoaffinity labeling of the cerebral sulfonylurea receptor using a novel radioiodinated azidoglibenclamide analogue. J. Neurochem. 1994;63:698-708.*

(Continued)

*Primary Examiner*—Unsu Jung
(74) *Attorney, Agent, or Firm*—Kagan Binder, PLLC

(57) ABSTRACT

Initiator polymers having an initiator group and a ligand group are provided. The initiator polymers are capable of specifically binding to a receptor on a surface. Using a macromer system, the initiator polymers are useful for the formation of a polymeric matrix on the surface of a material. In particular, initiator polymers are provided that have specificity to pancreatic β cells and can be used to encapsulate cells for transplantation and the treatment of diabetes.

30 Claims, 3 Drawing Sheets

U.S. PATENT DOCUMENTS

| | | | |
|---|---|---|---|
| 7,427,415 | B2 | 9/2008 | Scharp et al. |
| 2002/0165337 | A1* | 11/2002 | Wallace et al. .............. 528/373 |
| 2004/0202774 | A1 | 10/2004 | Chudzik |

OTHER PUBLICATIONS

Aguilar-Bryan, L. et al. Photoaffinity labeling and partial purification of the beta cell sulfonylurea receptor using a novel, biologically active glyburide analog. J. Biol. Chem. 1990;265:8218-8224.*

Kramer, W. et al. Direct photoaffinity labeling of the putative sulfonylurea receptor in rat beta-cell tumor membranes by [3H]-glibenclamide. FEBS Lett. 1988;229:355-359.*

Bayley, H. & Knowles, J.R. Photoaffinity labeling. Methods Enzymol. 1977;46:69-114.*

Mellott et al., "Release of protein from highly cross-linked hydrogels of poly(ethylene glycol) diacrylate fabricated by UV polymerization," Biomaterials 22, pp. 929-941 (2001).

Seyfert et al., "Adhesion of leucocytes to microscope slides as influenced by electrostatic interaction," Biomaterials 16, pp. 201-207 (1995).

Uludag, H., et al., *Technology of mammalian cell encapsulation*, Advanced Drug Delivery Reviews, vol. 42, pp. 29-64 (2000).

Hwang, J.S., et al, *Synthesis of sulfonylurea conjugated copolymer via Peo spacer and its in vitro short-term bioactivity in insulin secretion from islets of Langerhans*, Biomaterials, vol. 19, pp. 1189-1195 (1998).

Park, K.-H., et al., *Determination of the Specific Interaction between Sulfonylurea-Incorporated Polymer and Rat Islets*, J. Biochem., vol. 131, pp. 359-364 (2002).

Park, K.-H., et al., *Interaction of sulfonylurea-conjugated polymer with insulinoma cell line of MIN6 and its effect on insulin secretion*, J. Biomed. Mater. Res., 55:72-78 (2001).

Park, K.-H., et al., *Incorporation of sulfonylurea into sugar-carrying polymers and their effects on insulin secretion from MIN6 cells in a solution state*, J. Biomater. Sci. Polymer Edn., vol. 12, No. 8, pp. 911-920 (2001).

Gopalakrishnan, M., et al., *Pharmacological characterization of a 1,4-dihydropyridine analogue, 9-(3,4-dichlorophenyl)-3,3,6,6-tetramethyl-3,4,6,7,9,10-hexahydro-1,8(2H,5H)-acridinedione (A-184209) as a novel $K_{ATP}$ channel inhibitor*, British Journal of Pharmacology, vol. 138, pp. 393-399 (2003).

Hastedt, K. and Panten, U., *Inhibition of ATP-sensitive K+-channels by a sulfonylurea analogue with a phosphate group*, Biochemical Pharmacology, vol. 65, pp. 599-602 (2003).

Cruise, G.M., et al., *In Vitro and In Vivo Performance of Porcine Islets Encapsulated in Interfacially Photopolymerized Poly(Ethylene Glyco) Diacrylate Membranes*, Cell Transplantation, vol. 8, pp. 293-306 (1999).

* cited by examiner

LIGAND-COUPLED INITIATOR POLYMERS AND METHODS OF USE

FIELD OF THE INVENTION

The current invention relates to compounds useful for forming a polymeric matrix on the surface of a substrate. More specifically, the invention relates to initiator polymers that can specifically bind to a target surface and promote formation of a polymeric matrix on the surface.

BACKGROUND

The use of polymeric material for the encapsulation of cells and tissue offers great potential for the treatment of diseases and other medical indications. Particularly useful applications involve utilizing polymeric material for encapsulating tissues or cells for transplantation into a patient in order to provide therapy. Although various techniques for encapsulating mammalian cells have been known for a number of decades and have been used in research settings, only more recently cell encapsulation technologies have been applied for the potential treatment of diseases.

Cell encapsulation methods are generally aimed at surrounding a cell or group of cells with a material barrier in order to protect the transplanted encapsulated cells from host immune rejection. The material barrier around the cells ideally allows the cells to remain viable and to function properly in order to provide therapeutic value to the host. In order to perform this function, the material that is used to encapsulate the cells, which typically includes a polymeric compound, should be resistant to biodegradation and should be sufficiently permeable to allow for diffusion of cellular waste products, nutrients, and molecules involved in cellular responses. Preferably, the material barrier is not permeable to certain host molecules, such as immunoglobulins and complement factors that could contribute to the destruction of the foreign cells.

Advances in cell encapsulation technologies have been focused on improving the permselectivity, mechanical properties, immune protectivity, and biocompatibility of the material barrier that is formed around the cells. Various micro- and macroencapsulation techniques, including microencapsulation by polyelectrolyte complexation, thermoreversible gelation, interfacial precipitation, interfacial polymerization, and flat sheet and hollow fiber-based macroencapsulation have been studied and are reviewed by Uludag et al. *Adv. Drug Deliv. Rev.* 42:29-64 (2000).

One commonly used method for the encapsulation of cells is the alginate crosslinking method, which utilizes polyanionic alginate and polycationic polylysine polymers. Encapsulation by the alginate method typically occurs by the crosslinking of alginate via the $Ca^{2+}$ ion and the interaction of polylysine with the alginate molecules. Unfortunately, there are a number of problems associated with this approach to cell encapsulation. Such problems include the swelling of alginate microcapsules due to the presence of $Ca^{2+}$ in the inner alginate core, insufficient biocompatibility due to guluronic acid content in alginate/polylysine capsules, and insufficient mechanical strength of the alginate coating. Moreover, the process of alginate encapsulation is nonspecific and can result in the formation of microcapsules that do not contain the cells or cell groups intended to be encapsulated or that contain other non-target biological materials. Due to these problems, alternative methods for cell encapsulation have been investigated.

One promising alternative to alginate crosslinking is a method termed interfacial polymerization. Interfacial polymerization has the possibility of offering all of the advantages of the alginate encapsulation method for cellular encapsulation and its therapeutic applications, although there has been little done to investigate its potential. Interfacial polymerization generally involves the formation of a layer of polymerized material, such as synthetic or natural polymerizable polymers, on the surface of a biological substrate. The formation of the layer of polymeric material is generally promoted by the activation of a polymerization initiator, which is deposited on the surface of the biological substrate, in the presence of the polymerizable polymers.

Some polymerization initiators for use in interfacial polymerization methods have been demonstrated in U.S. Pat. No. 5,410,016 and U.S. Pat. No. 5,529,914. These patents describe depositing the polymerization initiator, eosin Y, on a cell membrane and then activating the initiator to promote polymerization of a macromer solution. However, the use of eosin Y, which is a relatively nonpolar, low molecular weight light-activated initiator dye, or compounds similar to eosin, presents many disadvantages for interfacial polymerization methods and also presents potential problems to subjects receiving transplanted encapsulated cells. For example, these dyes and other similar low molecular weight compounds present toxicity problems as they can penetrate into a cell and interfere with normal biochemical pathways. If penetrated into the cell, these dyes can cause free radical damage when activated by external sources of energy. Other drawbacks arise if the dye is able to diffuse out of the formed polymeric layer, thereby producing potential toxicity to a host organism. Dyes such as eosin also tend to aggregate in aqueous solution, thereby reducing the efficiency of the encapsulation process and introducing problems with reproducibility. Finally, in view of the limited efficiency of these dyes in initiating sufficient radical chain polymerization, it is often necessary to add one or more monomeric polymerization "accelerators" to the polymerization mixture. These accelerators also tend to be small molecules which are capable of penetrating the cellular membrane and have the potential to be cytotoxic or carcinogenic. Therefore, it is also desirable to minimize the use of these accelerators. In attempts to overcome the above problems, applicants have previously introduced novel interfacial polymerization reagents and techniques (see U.S. Pat. Nos. 6,007,833 and 6,410,044; herein incorporated by reference in their entirety).

Despite these teachings, improved initiators for interfacial polymerization methods are desired. The cell surface, to which the initiator polymer is targeted, is very complex and presents a challenge for the design of initiators that function in a desired manner. For example, the cell surface contains numerous surface proteins, some of which have carbohydrate groups containing charged moieties, such as sulfated proteoglycans and glycosaminoglycans. It is desirable to design initiators that localize to the biological surface but do not affect the physiology of the cell in a negative manner. For example, improved initiators should preferably promote the formation of a polymeric layer on the cell surface in an efficient manner without triggering any detrimental cellular processes, such as signaling pathways that lead to cell death.

In another aspect, it may also be desirable to have the interfacial polymerization reagents or polymeric layers formed by the initiators impart a desired effect on the cell. For example, having encapsulated pancreatic cells that produce insulin or having encapsulated thyroid cells produce parathyroid hormone can be of value to a patient in need of such a therapy. Such action may reduce or eliminate the need for the patient to take drugs that promote such an effect in vivo.

SUMMARY OF THE INVENTION

In one aspect, the invention provides a method for coating a surface. The method includes contacting the surface with a ligand-coupled initiator polymer. The initiator polymer includes a polymerization initiator group and a ligand group, and the ligand group can specifically bind to a receptor on the surface. The method also includes contacting the surface with a polymerizable material and then activating the initiator group of the ligand-coupled initiator polymer to cause polymerization of the polymerizable material on at least a portion of the biological surface.

The method typically involves coating a biological surface, such as the outer membrane of a cell. In one aspect, the invention provides a method for encapsulating pancreatic islets with a polymeric coating. According to this embodiment, the ligand group used for this purpose can be a sulfonylurea derivative, which can also be useful for stimulating the pancreatic β cells to secrete insulin.

In another aspect, the invention provides a ligand-coupled initiator polymer that includes a photoinitiator group that is selected from the group of light activated dyes, and a ligand group. The light activated dyes can be selected from the group consisting of acridine orange, camphorquinone, ethyl eosin, eosin Y, erythrosine, fluorescein, methylene green, methylene blue, phloxime, riboflavin, rose bengal, thionine, xanthine dyes, and the like. In another aspect, the initiator polymer comprises a hydrophilic backbone, such as a polyacrylamide backbone or a backbone having similar hydrophilic properties.

The invention further provides a kit that includes an initiator polymer and a polymerizable material such as a macromer.

DETAILED DESCRIPTION OF THE INVENTION

Figure 1:
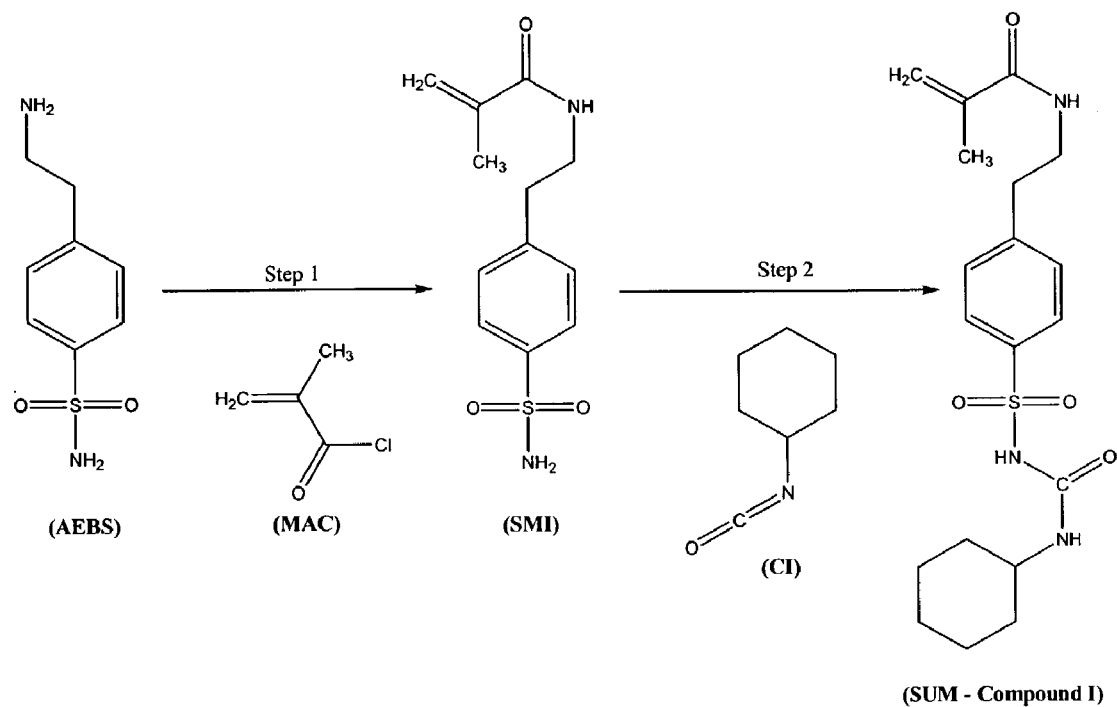
FIG. 1 illustrates a synthetic scheme for the preparation of a sulfonylurea monomer, SUM (Compound I).

The present invention provides ligand-coupled initiator polymers, herein referred to as "initiator polymers", compositions and systems including the initiator polymers, and methods for performing the interfacial polymerization of polymerizable material on a surface using these initiator polymers. "Polymer" refers to a compound having one or more different repeating monomeric units and includes linear polymers and copolymers, branched polymers and copolymers, such as highly branched dendrimer polymers and copolymers, herein referred to as "dendrimers", graft polymers and copolymers, and the like. The surface to which the initiator polymer binds generally bears a receptor that is able to associate with the ligand. In one embodiment of the invention the surface is a biological surface. As used herein "biological surface" broadly refers to the surface of any sort of biological material that has a surface receptor, such as, for example, the surface of cells, the surface of a group of cells, the surface of biological particles such as viral particles, or the surface of tissue. The initiator polymers of the invention are able to specifically interact with the receptor on the surface of the biological material and promote the polymerization of polymerizable material to form a polymeric layer, also referred to herein as a "polymeric matrix", on or near the biological surface.

The initiator polymers are particularly useful for cell encapsulation methods, although they can also be used to form a matrix of polymerized material on a biological surface having a receptor in any sort of ex vivo or in vivo method. Cell encapsulation involves the formation of a polymeric layer typically over the entire surface of the cell or cells, and this polymeric layer typically has certain physical and functional properties, such as thickness, permselectivity, strength, and protectivity. In other embodiments, the initiator polymers can be used to form a polymeric matrix of polymerized material on the surface of any type of natural or synthetic material that has specific receptors that can interact with the ligand group of the initiator polymer.

According to the invention, initiator polymers useful for providing a coating of a polymeric material on a surface include an initiator group and a ligand group. The initiator group refers to a portion of the initiator polymer that can specifically accept energy and generate a free radical species, directly or indirectly, and is sufficient to promote free radical polymerization of the polymerizable material. The ligand group refers to a portion of the initiator polymer that is able to specifically associate with a distinct receptor (for example, a ligand-binding member) on the surface of the material targeted for coating. The affinity between the ligand group and the receptor is generally high, typically having a dissociation constant $(K_d)$ in the range of $10^{-6}$ to $10^{-12}$ M.

In one embodiment, the ligand group of the initiator polymer is a molecule that can specifically associate with a therapeutically relevant receptor on the surface of a cell. Typically, a therapeutically relevant receptor is a receptor that can affect, either directly or indirectly, the function of a cell wherein the function is associated with changing a physical condition in a subject having the cell. For example, the binding of the ligand group to the receptor can trigger the production of a useful compound or can block the release of an undesirable compound. "Production" is used in its broadest sense and includes any cellular function that causes or increases the release of the therapeutic compound from the cell. In this particular embodiment, the ligand group of the initiator polymer serves a dual function. First, the ligand group specifically binds the initiator polymer to a specific receptor on the cellular surface, and second, the ligand group provokes a cellular response from the cellular material it is encapsulating. The cellular response can be initiated by the binding of the ligand group to its receptor, wherein the receptor moiety triggers the cell to produce a desired compound or compounds (or to elicit a desired cellular response). The invention also provides a novel way of initiating and maintaining a cellular response since the ligand group of the initiator polymer, which becomes incorporated into the polymer matrix formed via interfacial polymerization, remains in contact with the receptor on the cell surface following encapsulation. Therefore, the encapsulated cell can be continuously stimulated to produce the therapeutically useful compound. In one aspect, the ligand group is a molecule which can bind to the surface receptor on an endocrine cell and the binding causes the release of a compound that has an endocrine function in the body.

In a specific embodiment, the ligand group is a molecule that can bind a surface receptor on a pancreatic β cell. In some aspects, the binding of the molecule on the surface of the β cell can elicit a cellular response from the β cell, such as the production of insulin. In a preferred embodiment the ligand group is a sulfonylurea derivative, such as glyburide or a glyburide analogue. "Sulfonyl derivatives", as used herein, refers to compounds having a sulfonylurea portion and that are able to produce an insulinotropic effect. Sulfonylureas such as glyburide are ligands which can bind to potassium (ATP) channel proteins on the surface of pancreatic β cells.

The ligand-coupled initiator polymer of the invention is arranged to be soluble in an aqueous solution and able to associate with the receptor based on high affinity interactions between the ligand group and the receptor. In some embodiments the initiator group is non-polar and in some embodiments the ligand group is also non-polar. Therefore, typically, the initiator group and the ligand group will confer hydrophobic properties to the initiator polymer. In a preferred embodiment the initiator polymer can include a polymer backbone that is highly hydrophilic. A highly hydrophilic backbone can allow the initiator polymer to maintain its solubility and its receptor-binding properties in an aqueous environment.

In one embodiment, the initiator polymer can be used in a method for coating a biological surface, such as a cell encapsulation method. In these types of methods, the initiator polymer is used with a polymerizable material, such as macromers, that can form a matrix on the surface. In some embodiments the initiator polymer is placed in contact with the surface separately from the macromer component; in other embodiments the initiator polymer and the macromer component are placed in contact with the surface together as a polymerizable composition to the cells. Therefore, the invention also provides compositions that include a ligand-coupled initiator polymer and a polymerizable component. Other compounds useful for cell encapsulation, such as reductants/acceptors and viscosity enhancing agents can be introduced into the polymerization method in existing steps or in additional steps. Such reagents are described in detail below. Therefore, the invention also provides polymerizable compositions and kits for forming a polymer coating on a surface that can include a ligand-coupled initiator polymer, a polymerizable component, and other components that can enhance or that are useful for coating a surface, particularly for cell encapsulation.

In a more specific embodiment the invention provides for the ligand-coupled initiator polymer as a component in a group of compounds used for interfacial polymerization methods, and applicable for the treatment of particular diseases. These compounds and methods can be implemented for the encapsulation of cells or tissue, wherein the encapsulated cells or tissue are therapeutically useful. Cells or tissue of a particular type can be encapsulated and introduced into a subject in need of a certain type of cell or tissue. Endocrine cells, for example, are one class of cells that can be encapsulated using the initiator polymer of the invention and that can be therapeutically useful following administration to a patient having an endocrine-related disorder. Specific types of endocrine cells such as pancreatic islets can be encapsulated using the initiator polymer of the invention and transplanted to a diabetic patient in need of functional pancreatic tissue.

The ligand-coupled initiator polymer of the invention includes one or more ligand groups. As used herein, "ligand group" refers to any sort of chemical moiety that displays a specific binding interaction with a receptor on a surface. The receptor can be a molecule on a biological surface (e.g., a cell surface), for example, a protein or a carbohydrate. Ligand:receptor interactions exhibit binding specificity and typically exhibit effector specificity. Specific binding interactions of a ligand to a receptor are generally characterized as saturable. According to the invention, ligand:receptor dissociation constants ($K_d$) on the order of $10^{-6}$ to $10^{-12}$ M are typical of most specific binding interactions between the ligand and receptors as described herein.

The ligand group of the initiator polymer can allow for the specific localization and binding of the initiator polymer to the surface of a biological substrate such as a cell, group of cells, or tissue. Use of ligand groups allows for cell- or tissue-specific surface localization of the initiator polymer and the formation of a polymeric matrix on the surface of these specific target cells or tissues. In another aspect the ligand group can serve to promote a biological response as a consequence of the ligand:receptor interaction.

Examples of specific ligand:receptor interactions include small molecule:cell-surface receptor interactions such as sulfonylurea:sulfonylurea receptor and amiloride:amiloride-sensitive sodium channel protein (ENaC) interactions; and protein or peptide:cell-surface receptor interactions such as thyroid-stimulating hormone (TSH):thyroid plasma membrane receptor, vasopressin:vasopressin receptor, and antibody or antibody fragment:cell-surface antigen interactions. A receptor molecule can be any sort of surface determinant on a biological material, such as a portion of a membrane protein or a portion of a carbohydrate moiety attached to membrane proteins. The ligand can be chosen to bind various classes of cell surface receptors. Such classes include, for example, G-coupled receptors, ion-channel receptors, tyrosine kinase-linked receptors, and receptors with intrinsic enzymatic activity having one or multiple transmembrane domains.

The ligand group of the initiator polymer can be derived from any low molecular weight hydrophilic or lipophilic molecules; small charged molecules; water soluble peptides (peptide hormones); lipophilic hormones including erconsanoid hormones; antibodies or antibody fragments; proteins; and derivatives of any of the above.

The ligand group can have either an agonistic or antagonistic effect on the biological substrate. In one embodiment, the ligand group of the initiator polymer can bind to the receptor and elicit one or more biological responses, such as intercellular signal transduction and gene expression. Intercellular signal transduction can lead to, for example, changes in gene or protein expression, or changes in the modification or secretion of a particular compound, such as a protein, from the cell. In a preferred embodiment, the ligand is chosen to promote a biologically useful response from the biological material that it is in contact with. For example, the ligand group of the initiator polymer can bind a cell surface receptor and elicit production of a compound that is physiologically useful, or that is therapeutic for a particular physical condition. The ligand group pendent from the initiator polymer can exert its biological effect alone and/or when incorporated into the polymerized matrix that is formed after the initiator polymer is activated.

In one particular embodiment of the invention, the ligand group of the initiator polymer is a molecule capable of binding to a receptor on the surface of a pancreatic β cell. In some preferred embodiments, the ligand group is able to both bind the pancreatic β cell cell-surface receptor and stimulate an insulinotropic cellular response from the cells (for example, the production of insulin). The ligand group can be an insulinotropic agent able to cause the production and or release of insulin from the β cell. Therefore, according to the invention, an initiator polymer having a pancreatic cell-binding ligand can be placed in contact with and associated with a preparation of pancreatic islets and used to promote the formation of a matrix around the islets. Incorporated in the formed matrix is the initiator polymer containing the ligand group. The islets encapsulated within the matrix can be transplanted to a subject, and, because of the matrix, are immunoprotected and able to produce therapeutically useful compounds, such as insulin, that are able to produce an effect in the subject.

In one embodiment, the ligand group can associate with a portion of an ATP-sensitive potassium ($K^+$-ATP) channel, and can be, therefore, a $K^+$-ATP channel-binding ligand. Portions of the $K^+$-ATP channel can include, for example, $K^+$-ATP channel proteins such as sulfonylurea receptor proteins SUR1, SUR2, and pore-forming subunits such as KIR6.1 and KIR6.2. Particularly relevant portions of these proteins are those that can bind ligands which function to close the $K^+$-ATP channel. In pancreatic β cells $K^+$-ATP channel-closing ligands, a subgroup of $K^+$-ATP channel-binding ligands, can function to trigger insulin secretion from the cells. Typically this insulin secretion is caused by the $K^+$-ATP channel-closing ligands binding and preventing potassium efflux resulting in membrane depolarization and calcium influx causing release of the insulin from the cells.

$K^+$-ATP channel-closing ligands include first generation sulfonylureas such as tolbutamide, tolazamide, chlorpropamide, and acetohexamide; second generation sulfonylureas such as glimepiride, glipizide, and glyburide; insulin secretagogues such as meglitinide, repaglinide, nateglinide, prandin, and starlix; imidazoline-derived drugs such as midaglizole, LY397364, and LY389382; mitiglinide and analogues such as 5-chloro-N-(2-(4-hydroxyphenyl)ethyl)-2-methoxy-benzamide and 4-(2-(5-chloro-2-methoxybenzamido)ethyl) phenyl phosphate (Hastedt and Panten, *Biochem. Pharmacol.* 65:599 (2003)); 9-(3,4-dichlorophenyl)-3,3,6,6-tetramethyl-3,4,6,7,9,10-hexahydro-1,8(2H,5H)-acridinedione (Gopalakrishnan, M. et al. *Br. J. Pharmacol.* 138:393 (2003)); and functional derivatives thereof.

In another embodiment, the invention provides polymerizable monomers having a ligand group that can associate with a portion of a $K^+$-ATP channel. In particular, polymerizable monomers having an ethylenically unsaturated group and a ligand group having a sulfonylurea portion are provided by the invention.

The ligand groups can be coupled to the backbone of the initiator polymer in any suitable manner. For example, the ligand groups can be coupled to the backbone by preparing ligand-monomers and polymerizing the ligand-monomers with initiator-monomers. Synthesis of ligand-monomers can be readily accomplished using standard chemical reactions. Another method for preparing the initiator polymer involves preparing a reactive ligand moiety and reacting the ligand moiety with a reactive group on a preformed polymer. For example, an isocyanate or isothiocyanate derivative of a ligand group can be reacted with a polymer containing pendent amine groups thereby forming an initiator polymer bearing pendent ligand groups. The ligand groups can be coupled to and spaced in any suitable manner along the length of the polymer backbone, for example the ligand groups can be spaced in a random or ordered pattern along the length of the polymer backbone chosen or can be present primarily on one end of the polymer backbone.

The number of ligand groups coupled to the polymer backbone can be arranged to provide an initiator polymer that associates with the cell surface in a manner suitable to allow the formation of a polymeric material on the surface when the initiator polymer is activated. In one embodiment, the initiator polymer includes at least one ligand group. In another embodiment of the invention, the initiator polymer has up to about 5% of the monomeric units of the polymer coupled to ligand groups. In yet another embodiment the initiator polymer has up to about 10% of the monomeric units of the polymer coupled to ligand groups.

According to the invention, the ligand-coupled initiator polymer includes one or more initiator groups, which are coupled to the backbone of the initiator polymer. The initiator groups are able to promote free radical polymerization of polymerizable material, such as macromers, when energy capable of activating the initiator group is applied to the initiator polymer. Activated initiator groups can cause free radical polymerization of the polymerizable material either directly or indirectly. Indirect methods typically include the transfer of energy from the activated initiator to an acceptor or reductant, a chemical species that can form a free radical and can act to cause polymerization of the polymerizable material. In direct methods the initiator group provides the free radical itself.

According to the invention, the initiator polymer can be localized to a surface, such as the surface of a cell, via interaction of the ligand groups with the receptor on the surface. Upon activation of the initiator groups, polymerizable material that is in proximity to the initiator polymer polymerizes, leading to the formation of a layer of polymeric material, or a matrix, on the surface. This type of polymerization is typically referred to as interfacial polymerization.

The initiator polymer can include light-activated photoinitiator groups, thermally activated initiator groups, chemically activated initiator groups, or combinations thereof. Suitable thermally activated initiator groups include 4,4'azobis(4-cyanopentanoic) acid and 2,2-azobis[2-(2-imidazolin-2-yl) propane]dihydrochloride or other thermally activated initiators provided these initiators can be incorporated into an initiator polymer. Chemically activated initiation is often referred to as redox initiation, redox catalysis, or redox activation. In general, combinations of organic and inorganic oxidizers, and organic and inorganic reducing agents are used to generate radicals for polymerization. A description of redox initiation can be found in *Principles of Polymermization*, $2^{nd}$ Edition, Odian G., John Wiley and Sons, pgs 201-204 (1981). Redox initiators that are not damaging to biological systems are preferably used. Photoinitiator groups and thermally activated initiator groups that utilize energy that is not damaging to biological systems are preferably used. In one embodiment, photoinitiator groups having long wavelength UV and visible light-activated frequencies are coupled to the backbone of the initiator polymer. In a preferred embodiment, visible light-activated photoinitiators are coupled to the polymer backbone.

Photoinitiation can occur by various mechanisms, including Norrish type I reactions, intra- or intermolecular hydrogen abstraction reactions, and photosensitization reactions utilizing photoreducible or photo-oxidizable dyes. The latter two types of reactions are commonly used with an energy transfer acceptor or a reductant, which can be, for example, a tertiary amine. Such tertiary amines can be incorporated into the polymeric backbone of the macromer. In a preferred embodiment, the initiator polymer includes one or more initiator groups that allow for intra- or intermolecular hydrogen abstraction reactions or photosensitization reactions utilizing photoreducible or photo-oxidizable dyes when activated. Useful energy transfer acceptors or reductants for use with these types of initiators include, but are not limited to, tertiary amines such as triethanolamine, triethylamine, N-methyl diethanolamine, N,N-dimethyl benzylamine, tetramethyl ethylenediamine; secondary amines such as dibenzyl amine, N-benzyl ethanolamine, N-isopropyl benzylamine; and primary amines such as ethanolamine, lysine, and ornithine.

In one embodiment, photoinitiator groups having an absorbance of 350 nm and greater are used. More preferably, photoinitiator groups having an absorbance of 500 nm and greater are used. Suitable photoinitiator groups include light-activated initiator groups, such as long-wave ultra violet (LWUV) light-activatable molecules and visible light activatable molecules. Suitable long-wave ultra violet (LWUV) light-activatable molecules include, but are not limited to, [(9-oxo-2-thioxanthanyl)-oxy]acetic acid, 2-hydroxythioxanthone, and vinyloxymethylbenzoin methyl ether. Suitable visible light activatable molecules include, but are not limited to acridine orange, camphorquinone, ethyl eosin, eosin Y, erythrosine, fluorescein, methylene green, methylene blue, phloxime, riboflavin, rose bengal, thionine, xanthine dyes, and the like.

One common feature of these visible light activatable photoinitiator groups, and photoinitiator groups in general, is that of having a nonpolar portion. Due to the presence of this nonpolar portion, these photoinitiator groups generally have a low solubility in aqueous solutions. When these photoinitiator groups are coupled to another molecule, such as a polymer, the photoinitiator groups can confer nonpolar characteristics to the polymer conjugate and can generally reduce the solubility of the polymer conjugate in an aqueous solution.

The initiator polymer is coupled to a number of initiator groups in an amount sufficient to promote free radical polymerization of polymerizable material on a surface, such as the surface of a cell. The initiator polymer contains at least one and more typically a plurality of initiator groups. In some cases, the initiator polymer is highly loaded with initiator groups and can provide a high level of polymerization initiator activity. This may be desirable in cases wherein the number of receptor molecules on the surface of a cell is low and the highest polymerization potential per initiator polymer is desired. In another aspect, an initiator polymer highly loaded with initiator groups can be prepared and used in methods or compositions that include macromers that do not readily polymerize to form a polymeric layer. Accordingly, the invention provides ligand-coupled initiator polymers that are highly loaded with initiator groups.

According to the invention, the initiator polymer includes at least one initiator group. In another embodiment of the invention, the initiator polymer has up to about 5% of the monomeric units of the initiator polymer coupled to initiator groups. In yet another embodiment, about 10% of the monomeric units of the polymer are coupled to initiator groups. The initiator groups can be coupled to and pendent along the polymer backbone at any position and can be spaced in a random or ordered manner. The initiator groups preferably do not interfere with the ability of the initiator polymer to specifically associate with its receptor on a surface, such as a cell surface.

The initiator group can be coupled to the initiator polymer using any suitable method. In one method, for example, polymerizable monomers having initiator groups can be synthesized and subsequently used in a polymerization reaction to create an initiator polymer with pendent initiator groups. Synthesis of initiator-derivatized monomers can be readily accomplished using standard chemical reactions. For example, an isothiocyanate or an acid chloride analog of a photoinitiator group, such as a light-activated dye, can be reacted with an ethylenically unsaturated amine-containing monomer to form an initiator-derivatized monomer. In another method of preparing the initiator polymer, preformed polymers having reactive groups are reacted with initiator groups to attach the initiator groups to the preformed polymer. For example, an isothiocyanate analog of a photoinitiator can be reacted with a polymer having pendent amine groups thereby forming an initiator polymer having pendent initiator groups. Other synthetic schemes known to those skilled in the art can be employed to prepare the initiator polymer. These schemes are contemplated but will not be discussed in further detail.

In preferred embodiments the initiator polymer includes a plurality of initiator groups that are typically nonpolar. The presence of a plurality of initiator groups can confer substantial hydrophobic properties to the initiator polymer. Accordingly, this substantial hydrophobic property can be counter balanced by providing the initiator polymer with a hydrophilic backbone, which is discussed in detail below.

In a preferred embodiment of the invention, the ligand-coupled initiator polymer includes a ligand group, an initiator group, and is soluble in an aqueous solution. Generally, the initiator polymer includes a hydrophilic polymer backbone. The polymer backbone, which generally refers to the polymer chain without addition of any initiator group or ligand group, typically includes carbon and preferably one or more atoms selected from nitrogen, oxygen, and sulfur. The backbone can include carbon-carbon linkages and, in some preferred embodiments, can also include one or more of amide, amine, ester, ether, ketone, peptide, or sulfide linkages, or combinations thereof.

The polymeric backbone of the initiator polymer can include chemical groups useful for coupling the ligand group and the initiator group to the backbone to form the initiator polymer. Suitable chemical groups include acid (or acyl) halide groups, alcohol groups, aldehyde groups, alkyl and aryl halide groups, amine groups, amide groups, carboxyl groups, and the like. These chemical groups can be present either on a preformed polymer or on monomers used to create the ligand-coupled initiator polymer. Examples of polymers having suitable reactive or charged side group include polymers having reactive amine groups such as polylysine, polyomithine, polyethylenimine, and polyamidoamine dendrimers.

In one embodiment of the invention, the backbone of the initiator polymer provides the initiator polymer with hydrophilic properties. Preferred hydrophilic backbones include highly water-soluble polymers such as polyacrylamide. Examples of suitable polymer backbones include polyesters, polycarbonates, polyamides, polyethers (such as polyoxyethylene), polysulfones, polyurethanes, and copolymers containing representative monomer groups. Other suitable polymers include polyamines such as polyethylenimine, polypropylenimine, and the like, and polyamine polymers or copolymers formed from monomers such as 2-aminoethylacrylate, N-(3-aminopropyl)methacrylamide, and diallyl amine. In one preferred embodiment the backbone of the initiator polymer contains relatively few or no aromatic groups. Therefore, in one preferred embodiment of the invention, the initiator polymer includes (i) a polymerization initiator group, (ii) a ligand group, and (iii) a hydrophilic backbone.

In another aspect, the hydrophilic character of the initiator polymer can be improved by coupling charged groups to the polymer backbone. In these embodiments it is preferable that the initiator polymer is configured so that the presence of the charged groups does not interfere with the ability of the initiator polymer to associate with the target receptor on the surface of the substrate to be coated. Suitable charged groups include cationic groups such as quaternary ammonium, quaternary phosphonium, and ternary sulfonium groups. Suitable anionic groups that can be coupled to the initiator polymer include, but are not limited to, sulfonate, phosphonate, and carboxylate groups.

An initiator polymer having at least one initiator group and at least one ligand group can be prepared a variety of ways. For example, the initiator group and the ligand group can be attached to a "preformed" polymer or a copolymer that is reactive with the initiator and ligand groups. The preformed polymer or copolymer can be obtained from a commercial source or be synthesized from the polymerization of a desired monomer or combination of different monomers. In one example of preparing the initiator polymer, the initiator groups and the ligand groups are reacted with and attached to, for example, by covalent bonding, chemical groups pendent from the backbone of the polymer or copolymer. Such attachments of the initiator groups and the ligand groups can be achieved by, for example, substitution or addition reactions.

In another method of preparing the initiator polymer, monomers having initiator and monomers having ligand groups are first prepared. These initiator and ligand group-containing monomers are then co-polymerized to create an initiator polymer having both initiator and ligand groups. In some embodiments an individual monomer having both an initiator group and a ligand group can be used to prepare the initiator polymer. Optionally, other monomers that are not coupled to either an initiator or cationic groups can be polymerized with the ligand and initiator-coupled monomers to create the initiator polymer. A useful mixture of monomers for preparation of the initiator polymer includes up to about 10 wt % of a ligand-monomer, up to about 90 wt % of a hydrophilic monomer, and up to about 20 wt % of a monomer having a charged group. Methods of preparing the initiator polymer are exemplified below. Other standard methods known to those of skill in the art to prepare the initiator polymer are contemplated and will not be discussed further.

In one embodiment, the initiator polymer has (i) an amount of ligand groups that allow the initiator polymer to specifically associate with a receptor on a surface, (ii) an amount of initiator groups that can promote polymerization of a macromer on a surface, and (iii) a hydrophilic backbone of a size sufficient to solubilize the initiator polymer in an aqueous solution. In various embodiments, the initiator polymer has a weight average molecular weight ($M_w$) of greater than about 50 K Da, 100 K Da, 250 K Da, 500 K Da, 750 K Da, and 10,000 K Da. In some embodiments it is preferable that the initiator polymer has a $M_w$ in the higher ranges of these molecular weights recited.

As used herein "weight average molecular weight" or $M_w$, is an absolute method of measuring molecular weight and is particularly useful for measuring the molecular weight of a polymer (preparation), such as preparations of initiator polymers and macromers. Polymer preparations typically include polymers that individually have minor variations in molecular weight. Polymers are molecules that have a relatively high molecular weight and such minor variations within the polymer preparation do not affect the overall properties of the polymer preparation (for example, the characteristics of an initiator polymer preparation). The weight average molecular weight ($M_w$) can be defined by the following formula:

$$M_w = \frac{\sum_i N_i M_i^2}{\sum_i N_i M_i}$$

wherein N represents the number of moles of a polymer in the sample with a mass of M, and $\Sigma_i$ is the sum of all $N_i M_i$ (species) in a preparation. The $M_w$ can be measured using common techniques, such as light scattering or ultracentrifugation. Discussion of $M_w$ and other terms used to define the molecular weight of polymer preparations can be found in, for example, Allcock, H. R. and Lampe, F. W., *Contemporary Polymer Chemistry*; pg 271 (1990).

Therefore, in one specific embodiment of the invention, the initiator polymer includes (i) a plurality of polymerization initiator groups, (ii) a ligand group, and (iii) a hydrophilic backbone, wherein the $M_w$ of the initiator polymer is greater than about 50K Da, more preferably greater than about 100 K Da, and most preferably greater than about 250 K Da.

In another specific embodiment of the invention, the initiator polymer includes (i) a plurality of photoinitiator groups selected from the group of visible light-activated dyes, (ii) a ligand group, and (iii) a hydrophilic backbone, wherein the $M_w$ of the initiator polymer is greater than about 50 K Da, more preferably greater than about 100 K Da, and most preferably greater than about 250 K Da.

In yet another specific embodiment of the invention, the initiator polymer includes (i) a plurality of photoinitiator groups selected from the group of visible light-activated dyes, (ii) a $K^+$-ATP channel-binding ligand group, and (iii) a hydrophilic backbone, wherein the $M_w$ of the initiator polymer is greater than about 50 K Da, more preferably greater than about 100 K Da, and most preferably greater than about 250 K Da.

The ligand-coupled initiator polymer can promote the polymerization of polymerizable material, such as macromers, on a surface having a ligand-binding receptor. A matrix of polymeric material is formed on the surface after the initiator polymer is activated. The polymerizable material can be any sort of compound, including monomers and polymers having one or more polymerizable groups. Polymerizable groups are portions of the polymerizable compounds that are able to propagate free radical polymerization, such as carbon-carbon double bonds. Preferred polymerizable groups are found in polymerizable compounds having vinyl or acrylate groups. More specific polymerizable portions include acrylate groups, methacrylate groups, ethacrylate groups, 2-phenyl acrylate groups, acrylamide groups, methacrylamide groups, itaconate groups, and styrene groups. Preferred materials for the encapsulation of cellular material are biocompatible polymerizable polymers (also referred to as macromers). Such macromers can be straight chain or branched polymers or copolymers, or graft copolymers. Synthetic polymeric macromers, polysaccharide macromers, and protein macromers suitable for use with the initiator polymer of the current invention are described in U.S. Pat. No. 5,573,934 (Hubbell et al.), the teaching of which is incorporated in its entirety by reference.

Preferred macromers include, but are not limited to, polymerizable poly(vinylpyrrolidone) (PVP), poly(ethylene glycol) (PEG), poly(ethylene oxide) poly(ethyloxazoline), poly (propylene oxide), polyacrylamide (PAA), poly(vinyl alcohol) (PVA), copolymers thereof, and the like. In particular, PEG and PAA are more preferred macromers. These types of macromers are typically soluble in water and are more stable in vivo as compared to biodegradable polymers.

In some cases it may be desirable to use naturally occurring or synthetic macromers as the polymerizable material. Suitable macromers include naturally occurring polymers such as polysaccharides, examples of which include, but are not limited to, hyaluronic acid (HA), starch, dextran, heparin, and chitosan; and proteins (and other polyamino acids), examples of which include, but are not limited to, gelatin, collagen, fibronectin, laminin, albumin, and active peptides thereof. In order to make these naturally occurring or synthetic macromers polymerizable, polymerizable groups can be incorporated into a polymer using standard thermochemical reactions. For example, polymerizable groups can be added to collagen via reaction of amine containing lysine residues with acryloyl chloride. These reactions result in collagen containing polymerizable moieties. Similarly, when synthesizing a macromer, monomers containing reactive groups can be incorporated into the synthetic scheme. For example, hydroxyethylmethacrylate (HEMA) or aminopropylmethacrylamide (APMA) can be copolymerized with N-vinylpyrrolidone or acrylamide yielding a water-soluble polymer with pendent hydroxyl or amine groups. These pendent groups can subsequently be reacted with acryloyl chloride or glycidyl acrylate to form water-soluble polymers with pendent polymerizable groups. Suitable synthetic polymers include hydrophilic monomers containing degradable segments as described in U.S. Pat. No. 5,410,016 supra, the teaching of which is incorporated in its entirety by reference.

In another aspect, the invention provides a polymerizable composition that includes a ligand-coupled initiator polymer and a macromer. The polymerizable composition can also include other compounds useful cell encapsulation methods such as reductant/acceptors and viscosity-enhancing agents, for example, polyethylene glycols, and glycerol. Therefore, in one embodiment, the invention provides a polymerizable composition that includes: (i) an initiator polymer having at least one polymerization initiator group and a ligand group that is capable of interacting with a receptor on a surface, and (ii) a macromer. In a more specific embodiment the invention provides a polymerizable composition that includes: (i) an initiator polymer having photoinitiator group selected from the group of visible light-activated dyes, and a ligand group able to interact with a receptor on a surface, and (ii) a macromer.

Cell Encapsulation Methods

As previously indicated, the initiator polymer of the invention is typically used with macromers and, in some cases, a reductant/acceptor in a method to provide a coating to a biological surface. The reagents are particularly suitable for cell encapsulation processes.

Cells or tissue to be encapsulated can be obtained from an organism, for example, a human donor, or obtained from a cell culture, which can be transformed or otherwise modified. Specific types of cells and tissue that can be encapsulated and used for the treatment of diseases are discussed below. "Cells" refers to individual membrane-bound biological units that can be present as part of a tissue or organ, or can function independently as micro-organisms. "Tissue" refers to a biological mass that includes groups of similar cells, and also typically includes extracellular material that is associated with the cells. Cells, or tissue in particular, can be subject to treatment prior to the encapsulation process. For example, tissue can be treated with enzymatic or other suitable reagents, such as trypsin, hyaluronidase, or collagenase, to obtain individual cells or cell groups of a suitable size for the encapsulation process. Alternatively, tissue can be subject to mechanical processes in order to prepare suitable cellular starting material. Prior to encapsulation cells can also be treated with drugs, prodrugs, hormones, or the like, or can be cultured to provide cells that display a desired expression pattern or have a certain morphological features. Technical references that provide detailed instructions for the preparation of cells or tissue and the treatment of prepared cells or tissue are available and can be found in, for example, in *Basic Cell Culture Protocols*, Pollard, J. W. and Walker, J. M., Ed. (1997).

Alternatively, cells or tissue suitable for encapsulation and intended for use with the ligand-coupled initiator of the invention can be commercially obtained. For example, viable human liver preparations such as microsomes and hepatocytes, and viable human pancreatic preparations such as pancreatic islets, can be obtained from commercial sources such as CellzDirect, Inc. (Tucson, Ariz.).

With information available in technical literature, one can utilize the ligand-coupled initiator polymer in methods for coating a surface, and in particular, in the novel and inventive methods as described herein for encapsulating cells and tissue. For example, the teaching Cruise, et al., *Cell Transplantation* 8:293 (1999), can provide a basis for the cell encapsulation methods using the ligand-coupled initiator polymer of the invention. Cells or tissue suitable for the encapsulation process, prepared as indicated above or obtained from a commercial source, can be suspended in a suitable solution, such as a biocompatible buffered aqueous solution, such as, for example Roswell Park Memorial Institute (RPMI) media. Other reagents can be added to this solution, such as animal serum; proteins such as albumin; oxidants; reductants; vitamins; minerals; growth factors; or other components that can have an impact on the viability and function of the cells or tissues.

The ligand-coupled initiator polymer can be added to this solution before or after contacting the cells or tissue with the solution. The initiator polymer can be brought into contact with the cells in an amount that is sufficient for formation of a matrix around the cells or tissue. In one embodiment, the concentration of the initiator polymer is from 0.001 to 0.5 wt %. In yet another embodiment, the concentration of the initiator polymer is from 0.1 to 0.25 wt %. In one embodiment the initiator polymer is brought in contact with the cells for a period of time that is sufficient for the initiator polymer to associate with the surface of the cells. Optionally, a washing step can be performed. This washing step can be used, for example, to remove excess unbound initiator or other material in contact with the cells. After the initiator polymer is brought in contact with the cells or tissue, the polymerizable material, such as macromers, can be brought in contact with the cells. In another embodiment, the initiator polymer is brought into contact with the cells or tissue together with the polymerizable material. In yet another embodiment the polymerizable material is brought into contact with the cells prior to bringing the initiator polymer into contact with the cells.

The polymerizable material (e.g., macromers) can be brought into contact with the cell or tissue in an amount that allows formation of a matrix of a desired thickness. A concentration of macromer in solution useful for cell encapsulation can be in the range of 5-50 wt %, and more preferably in the range of 10-30 wt %. In some embodiments, the polymerizable material can be placed in contact with the cells for a period of time prior to activating the ligand-coupled initiator polymer.

Other reagents can be brought in contact with the cells or tissue during the encapsulation process. As previously mentioned, such reagents include acceptors or reductants, such as tertiary amines (e.g., triethanolamine) that can form a free radical and cause free radical polymerization of the polymerizable material. Suitable acceptors or reductants are known in the art and are commercially available. These acceptors or reductants are typically used in indirect polymerization methods wherein the initiator group transfers energy to the acceptors or reductants to promote free radical polymerization of the polymerizable material. Reagents such as viscosity-enhancing reagents can also be used in the method of the invention. Viscosity-enhancing reagents can improve the process of polymerization. Suitable viscosity-enhancing reagents are known in the art and are commercially available. One of skill in the art can determine suitable amounts of any of these additional reagents for performing the encapsulation process.

After the reagents necessary to promote formation of a matrix are brought in contact with the surface to be coated, a source of energy, such as a thermal or electromagnetic energy sufficient to activate the initiator group, is applied to initiate polymerization of the polymerizable material. Long-wave ultra violet (LWUV) and visible wavelengths in range of 350 nm to 900 nm are preferred and can be supplied by lamps and laser light sources. Lamps or laser light sources that can provide these wavelengths of light are commercially available and can be obtained from, for example, EFOS Inc. (Mississauga, Ontario, Canada). A particularly suitable wavelength for use with the preferred initiator polymers of the invention is about 520 nm. The time and temperature of the reaction are maintained to provide a desired coating. For example, the cells or tissue in contact with the initiator polymer and macromer can be treated with light for a period in the range of seconds to minutes. The polymerization reaction can be terminated by removing the light source. The encapsulated cells or tissue can then be subject to further treatment if desired. For example, it may be desirable to concentrate the encapsulated material, for example, by centrifugation, prior to introducing the encapsulated material into a subject.

As indicated, a number of technical references that provide detailed procedures for encapsulating cells are available and can provide a framework for which the ligand-coupled initiator polymer can be used. Therefore using the available information, one can perform surface coating of a material, more specifically, the encapsulation of cellular material and tissue using the ligand-coupled initiator polymer and reagents described herein or in other references.

Treatment

According to the invention, the initiator polymer can be used to promote the formation of a matrix of polymerized material on a biological surface. Polymerization using the initiator polymer can be performed in vivo by applying an initiator polymer and polymerizable material, either together or separately, to a subject in either an invasive or in a noninvasive procedure. Other particularly useful applications involve the ex vivo encapsulation of cells or tissue. In this application cells or tissue can be obtained from a suitable source, encapsulated with a matrix of polymeric material using a composition including the initiator polymer described herein, and then introduced into a subject in need of the encapsulated cells or tissue. In some cases, after receiving the transplanted encapsulated cells, the subject can be administered a pharmaceutical agent, such as a compound that is different than the compound used as the ligand group of the initiator polymer, that can penetrate the matrix that encapsulates the cells and can provoke a cellular response which is of therapeutic value to the subject. This type of ex vivo encapsulation and transplantation procedure is advantageous as it can provide a matrix coating affording the transplanted cells protection from host immune rejection while allowing the encapsulated cells to provide a therapeutic value to the host.

In one aspect of the invention, the initiator polymer is used to encapsulate cells or tissue from glands and organs of the endocrine system, which include cells from the pituitary gland; cells from the adrenal gland; cells from the thyroid/parathyroid glands; cells from the pancreatic islets, such as beta cells, alpha cells, delta cells, and pancreatic polypeptide (PP) cells; cells from the liver; and cells from reproductive glands such as the testis and ovary. Endocrine cells can be removed from a donor individual and encapsulated with polymeric material using the initiator polymer as described herein.

Encapsulated endocrine cells can be transplanted to an individual having any of the following conditions or needs: a pituitary disorder and in need of growth hormone (GH), adrenocorticotropic hormone (ACTH), follicle stimulating hormone (FSH), leutinizing hormone (LH), thyroid stimulating hormone (TSH), oxytocin, or antidiuretic hormone (ADH); an adrenal disorder and in need of mineralcorticoids (for example, aldosterone) glucocorticoids (for example, cortisol), androgenic steroids, or catecholamines such as epinephrine or norepinephrine; a thyroid or parathyroid disorder and in need of thyroxin, calcitonin, or parathyroid hormone (PTH); a pancreatic disorder such as diabetes and in need of insulin, glucagon, somatostatin, or pancreatic polypeptide; a liver disorder and in need of bile or plasma proteins, including clotting factors; a reproductive gland disorder and in need of male hormones such as testosterone or female hormones such as estrogen.

Other types of cells that can be encapsulated include immature and mature cells from the cardiovascular, respiratory, renal, nervous, muscular, and skeletal systems. In some aspects cells that have been transformed or genetically modified can be encapsulated and transplanted into a host. For example, cells that have been transformed or modified to produce a therapeutically useful compound, such as a peptide hormone or an enzyme can be encapsulated and introduced into an individual.

The invention also specifically provides interfacial polymerization compounds, compositions, and methods for the treatment of diabetes. In particular, the invention provides for initiator polymers useful for the binding to and promoting the interfacial polymerization of a biocompatible polymeric layer around pancreatic β cells and islets. At the same time, the use of the initiator polymer to provide the polymeric layer stimulates a desirable cellular response by potentiating an increased insulin production from the cells.

As stated above, in some instances, a pharmaceutical agent can be administered to the subject after transplantation of the encapsulated cells. The pharmaceutical agent can provoke a therapeutically useful cellular response from the encapsulated cells if needed. Other drugs that can stimulate insulin production and that can be coadministered with the transplanted encapsulated β cells include metformin, acarbose, and troglitazone. Other useful drugs include that can be administered to subjects having encapsulated cells include antithrombogenic, anti-inflammatory, antimicrobial, antiproliferative, and anticancer compounds, as well as growth factors, morphogenic proteins, and the like.

In another aspect, the initiator polymer and polymerizable material can also be used in in vivo applications to provide artificial barriers, for example, barriers to prevent tissue adhesion following surgery. For this application, the initiator polymer along with polymerizable material is applied to the surface of the tissue. The composition is then illuminated to initiate polymerization and a barrier matrix is formed. The polymeric matrix prevents other tissue from adhering to the coated tissue. In some procedures a polymeric matrix can be formed on the surface of a blood vessel to prevent blood factors or cells, such as platelets, from interacting with or adhering to the blood vessel wall. Both degradable and non-degradable macromer systems can be used for this purpose.

The initiator polymer of the invention can also be utilized for other medically useful purposes. For example, the initiator polymer can be a component used for forming adhesives for tissue and other surfaces. In another example, the initiator polymer can be applied to a surface bearing a receptor, to which adhesion is desired. The surface can be washed to remove any unbound or excess initiator polymer and a polymerizable material can be added. Another surface can be contacted with the initiator polymer-coated surface and then a source of energy can be applied to activate the initiator polymer and to polymerize the polymerizable material, thereby forming a surface-to-surface junction. If a temporary adhesive is desired, the polymerizable material can include a degradable material, for example, biodegradable macromers.

The initiator polymer can also be used for the formation of barriers on surfaces bearing a receptor. An example of such an application is a barrier for the prevention of tissue adhesion following surgery. For this application, an initiator polymer can be applied to the surface of damaged tissue. The surface can be washed to remove unbound or excess initiator polymer, and a polymerizable material can then be added. The initiator polymer can then be activated on the surface to polymerize the polymerizable material. The polymeric matrix formed by this polymerization can prevent other tissue from adhering to the damaged tissue. Both degradable and/or non-degradable macromers can be used in this barrier formation method.

The invention will now be demonstrated referring to the following non-limiting examples.

TABLE I
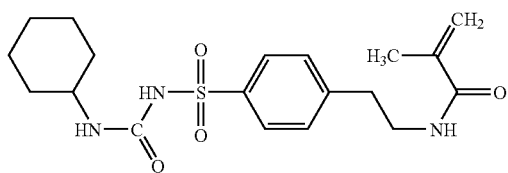
(Compound I: SUM)
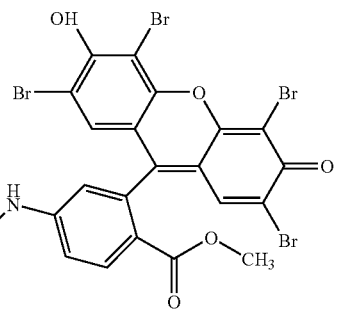
(Compound II: EITCM)
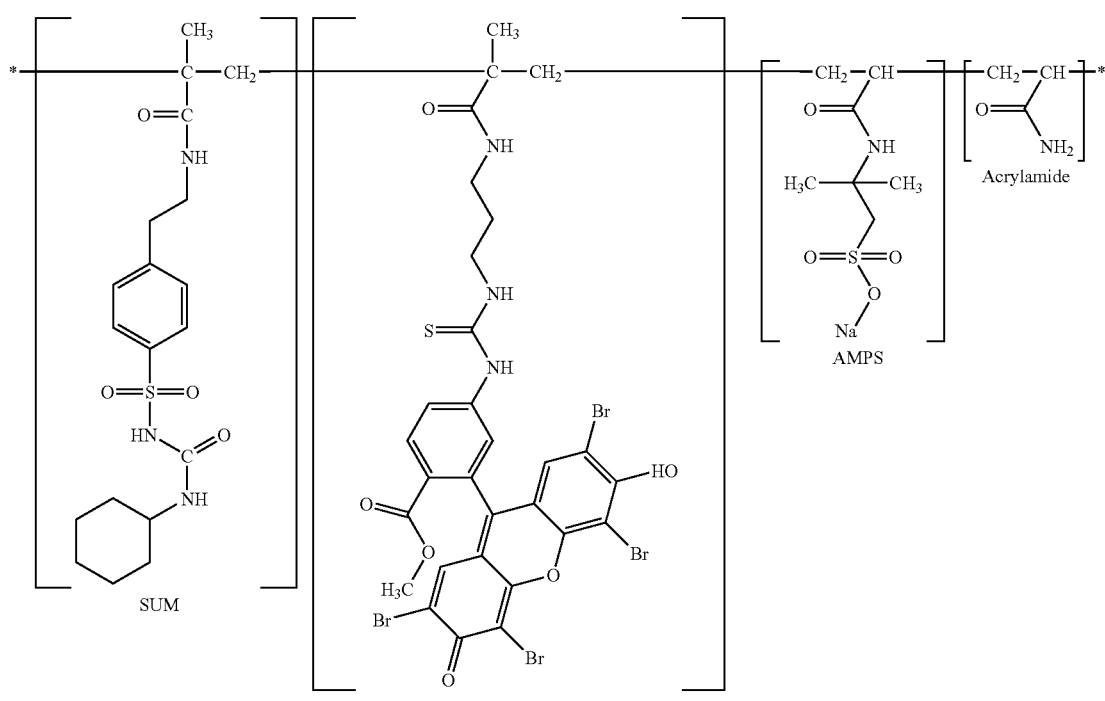
(Compound III: SEAA Initiator Polymer)
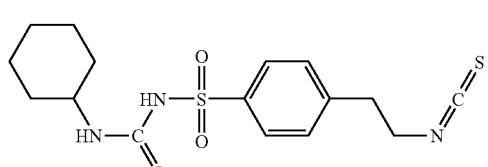
(Compound IV: SUNCS)

TABLE I-continued

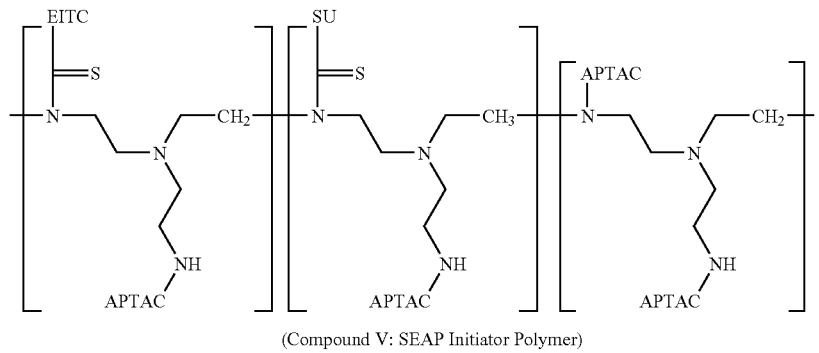

(Compound V: SEAP Initiator Polymer)

EXAMPLES

Example 1

Synthesis of a Sulfonylurea Monomer (SUM)

Preparation of a monomer having a sulfonylurea ligand portion is achieved according to the synthetic scheme as illustrated in FIG. 1. A solution of 4-(2-aminoethyl)benzenesulfonamide (AEBS) and triethylamine (TEA) in chloroform (or acetonitrile) is cooled in an ice bath. As illustrated in step 1 of FIG. 1, to the cooled stirred AEBS solution is added a solution of methacryloyl chloride (MAC), in chloroform (or acetonitrile). After the addition is completed, the reaction is stirred at room temperature for 2 hours. The volatile organic materials are removed under vacuum with an air bleed to avoid polymerization. The residue (sulfamoyl monomer intermediate (SMI): 2-methyl-N-(2-(4-sulfamoyl-phenyl)-ethyl)-acrylamide) is dissolved in an aqueous sodium hydroxide solution. As illustrated in step 2, to the aqueous solution is added a solution of cyclohexyl isocyanate (CI) in acetone (or acetonitrile), and the resultant reaction is stirred at room temperature for 16 hours. Finally, the reaction is acidified with HCl and the precipitate is isolated and dried to give the sulfonylurea monomer (Compound I: SUM), which is also shown in Table I.

Example 2

Synthesis of an EITC Monomer (EITCM)

Figure 2:
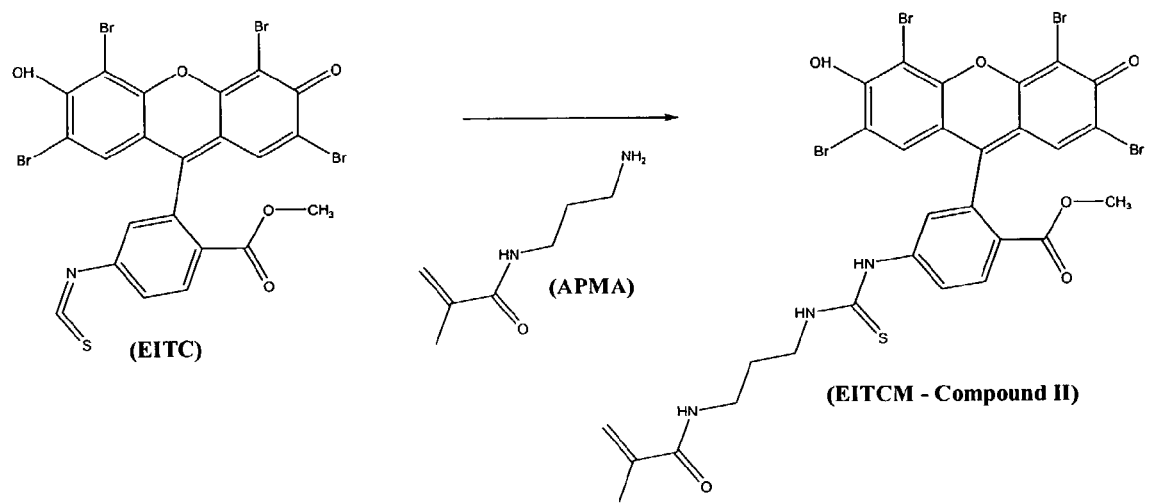
FIG. 2 illustrates a synthetic scheme for the preparation of an EITC Monomer, EITCM (Compound II).

Preparation of a monomer having an EITC photoinitiator portion is achieved according to the synthetic scheme as illustrated in FIG. 2. To a solution of eosin isothiocyanate (EITC; 4-Isothiocyanato-2-(2,4,5,7-tetrabromo-6-hydroxy-3-oxo-3H-xanthen-9-yl)-benzoic acid methyl ester) in dimethylsulfoxide (DMSO) is added a solution of N-(3-aminopropyl)methacrylamide (APMA) in chloroform. The solution is stirred at room temperature for 16 hours. The chloroform is removed under vacuum with an air bleed. EITCM in a DMSO solution is used in the preparation of an initiator polymer in Example 3. EITCM (Compound II) is also shown in Table I.

Example 3

Preparation of a SUM-EITCM-AMPS-Acrylamide (SEAA) Initiator Polymer

The initiator polymer, which can be represented by Compound III as illustrated in Table I, is prepared by placing SUM, EITCM, AMPS (sodium 2-acrylamido 2-methyl propane sulfonate), mercaptoethanol, AIBN (2,2'-azobisisobutyronitrile) and DMSO (dimethylsulfoxide) in a glass vessel and polymerizing the mixture. The solution is degassed (deoxygenated), blanketed with argon and heated at 55° C. with stirring for 16 hours. The DMSO solution containing the polymer product is placed in 12-14 kDa molecular weight cut off (MWCO) dialysis tubing and dialyzed against deionized water. The product is then isolated by lyophilization.

Example 4

Synthesis of a Sulfonylurea-isothiocyanate (SUNCS)

Figure 3:
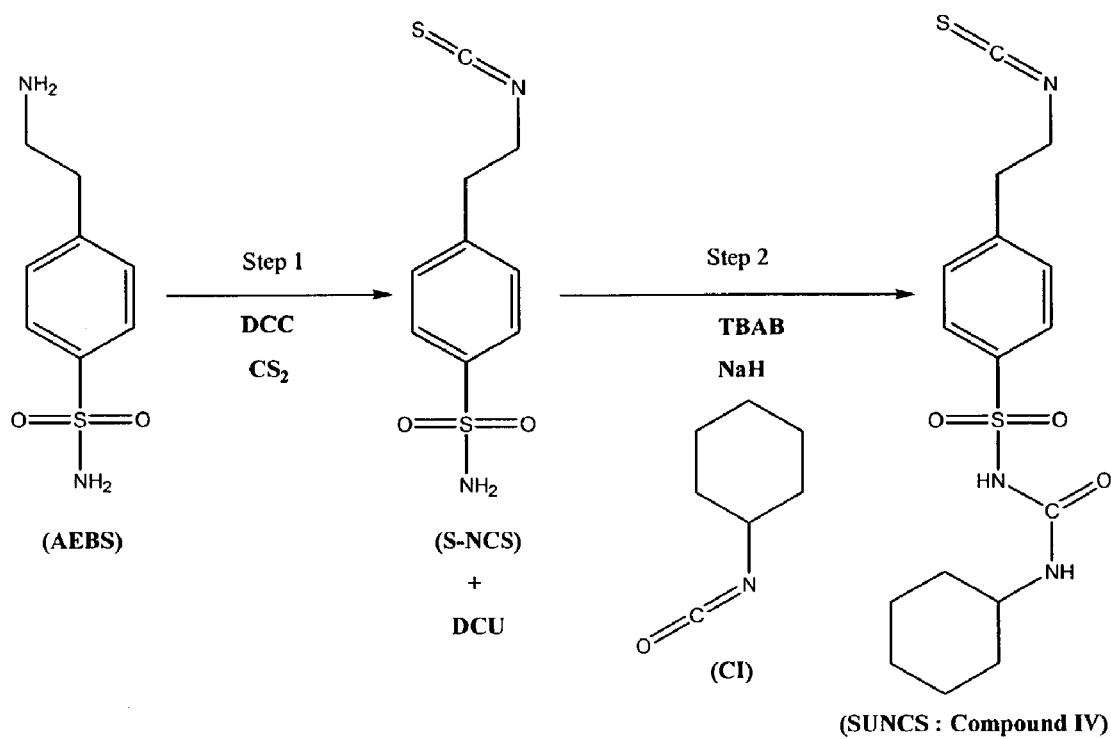
FIG. 3 illustrates a synthetic scheme for the preparation of a sulfonylurea derivative, SUNCS (Compound IV).

A sulfonylurea derivative (SUNCS) is synthesized in preparation for making another sulfonylurea-containing initiator polymer. The preparation of SUNCS is achieved according to the synthetic scheme as illustrated in FIG. 3. 4-(2-Amino-ethyl)benzenesulfonamide (AEBS) is first dissolved in acetonitrile (or chloroform). In step 1 the AEBS solution is reacted with carbon disulfide ($CS_2$) and dicyclohexylcarbodiimide (DCC). Dicyclohexylurea (DCU) product is removed from sulfamoyl-isothiocyanate (S-NCS) by filtration. The solvents are then removed to give the S-NCS intermediate. In step 2 the S-NCS, cyclohexyl isocyanate, and tetrabutylammonium bromide (TBAB) are placed in a glass vessel with tetrahydrofuran (THF) and the mixture is stirred under an inert dry atmosphere during the slow addition of sodium hydride (NaH). The SUNCS product (Compound IV, also shown in Table I) is then isolated and purified by flash chromatography.

Example 5

Preparation of a SUNCS-EITC-APTAC-PEI (SEAP) Initiator Polymer

A SEAP initiator polymer is prepared according to the following procedure. DMSO solutions containing eosin isothiocyanate (EITCNCS; Sigma-Aldrich Corp., St. Louis, Mo.), acrylamido propyltrimethyl ammonium chloride (APTAC; Sigma-Aldrich Corp., St. Louis, Mo.) and SUNCS are first individually prepared. A solution containing polyamine polyethylenimine (PEI) having a $M_w$ of 10,000 Da is prepared by dissolving the PEI in DMSO. To the PEI solution is added the EITCNCS, APTAC, and SUNCS solutions. The reaction is stirred for 16 hours at room temperature. The polymerization product is purified using 5,000 MWCO dialysis tubing and the product is isolated by lyophilization. The final product can be represented by Compound V in Table I wherein EITC represents eosin, APTAC represents acrylamido propyltrimethyl ammonium chloride, and SU represents sulfonylurea.

We claim:

1. A method for encapsulating cells comprising the steps of
   a) providing cells having a surface receptor;
   b) contacting the cells with an initiator polymer comprising:
      i) a polymeric backbone;
      ii) at least five initiator groups pendent from the polymeric backbone;
      iii) a ligand group pendent from the polymeric backbone that specifically binds to the surface receptor on the surface of the cells; and
      iv) charged groups pendent from the polymeric backbone;
   c) contacting the surface of the cells with a polymerizable material; and
   d) activating the initiator groups of the initiator polymer to cause polymerization of the polymerizable material and formation of a layer of polymerized material on the surface of the cells.

2. The method of claim 1 wherein the ligand group comprises a $K^+$-ATP channel-binding ligand.

3. The method of claim 2 wherein the ligand group comprises a $K^+$-ATP channel-closing ligand.

4. The method of claim 3 wherein the ligand group comprises a sulfonylurea derivative.

5. The method of claim 4 wherein the sulfonylurea derivative is a selected from the group consisting of tolbutamide, tolazamide, chlorpropamide, acetohexamide, glimepiride, glipizide, and glyburide.

6. The method of claim 1 wherein the binding of the initiator polymer to a surface receptor on the pancreatic β cell causes the cell to secrete insulin.

7. The method of claim 1 wherein the polymeric backbone is hydrophilic.

8. The method of claim 7 wherein the hydrophilic backbone is a polyacrylamide backbone.

9. The method of claim 1 wherein the initiator group comprises a photoinitiator.

10. The method of claim 9 wherein the photoinitiator has an excitation wavelength of 350 nm or greater.

11. The method of claim 10 wherein the photoinitiator has an excitation wavelength of 500 nm or greater.

12. The method of claim 11 wherein the photoinitiator is selected from the group consisting of acridine orange, camphorquinone, ethyl eosin, eosin Y, erythrosine, fluorescein, methylene green, methylene blue, phloxime, riboflavin, rose bengal, thionine, and xanthine dyes.

13. The method of claim 1 wherein the initiator polymer has a $M_w$ of about 50 K Da or greater.

14. The method of claim 13 wherein the initiator polymer has a $M_w$ of about 100 K Da or greater.

15. The method of claim 1 where, in step b), the ligand group and the receptor have a dissociation constant in the range of $10^{-6}$ to $10^{-12}$ M.

16. The method of claim 1 wherein the ligand group has specificity for a receptor on the surface of an endocrine cell.

17. The method of claim 16 wherein the ligand group has specificity for a receptor on the surface of a pancreatic β cell.

18. The method of claim 1 wherein the charged group is selected from cationic groups consisting of quaternary ammonium, quaternary phosphonium, and ternary sulfonium groups or anionic groups consisting of sulfonate, phosphonate, and carboxylate groups.

19. A method for encapsulating pancreatic islets with a polymeric coating comprising the steps of:
   a) providing pancreatic islet cells;
   b) contacting a surface of the cells with an initiator polymer comprising:
      i) a hydrophilic backbone;
      ii) a plurality of photoinitiator groups pendent from the hydrophilic backbone, the photoinitiator groups selected from the group consisting of visible light-activated dyes;
      iii) a ligand group pendent from the hydrophilic backbone, the ligand group comprising a sulfonylurea derivative that specifically binds to a receptor on the surface of the pancreatic islet cells; and
      iv) charged groups pendent from the polymeric backbone;
   c) contacting the surface of the pancreatic islet cells with a polymerizable material comprising macromers; and
   d) activating the photoinitiator groups to cause polymerization of the macromers, which forms a layer of polymerized macromers on the surface pancreatic islet cells.

20. The method of claim 19 wherein the sulfonylurea derivative is selected from the group consisting of tolbutamide, tolazamide, chlorpropamide, acetohexamide, glimepiride, glipizide, and glyburide.

21. The method of claim 19 wherein the molecular weight of the initiator polymer is greater than 50 K Da.

22. The method of claim 21, wherein the step of contacting, the initiator polymer is present in a composition at a concentration in the range from 0.001 to 0.5 wt %.

23. The method of claim 19 wherein the photoinitiator groups comprise eosin groups.

24. The method of claim 19 wherein the initiator polymer is prepared by copolymerizing a mixture of monomers, wherein up to 10% of the monomers in the mixture comprise pendent photoinitiator groups.

25. The method of claim 24 wherein up to 5% of the monomers in the mixture comprise pendent photoinitiator groups.

26. The method of claim 19 wherein the hydrophilic backbone comprises polyacrylamide.

27. The method of claim 19 wherein the hydrophilic backbone comprises polyethyleneimine.

28. The method of claim 19 wherein the initiator polymer is prepared by copolymerizing a mixture of monomers, wherein up to 10% of the monomers in the mixture comprise pendent ligand groups.

29. The method of claim 28 wherein up to 5% of the monomers in the mixture comprise pendent ligand groups.

30. Encapsulated cells formed according to the method of claim 1, the encapsulated cells comprising
   a) an initiator polymer comprising:
      i) a polymeric backbone;
      ii) at least five initiator groups pendent from the polymeric backbone;
      iii) a ligand group pendent from the polymeric backbone that specifically binds to a receptor on the surface of the cells, and
      iv) charged groups pendent from the polymeric backbone, wherein
   the initiator polymer is bound to the receptor on the surface of the cells via the ligand group, and
   b) a layer of polymerized material on the surface of the cells.

* * * * *